United States Patent

Davis et al.

[11] Patent Number: 5,087,254
[45] Date of Patent: Feb. 11, 1992

[54] ABSORBENT PRODUCTS HAVING INTEGRAL TRANSVERSE RETAINING TAB AND POCKET

[75] Inventors: Martha Davis, New York, N.Y.; Daniel Formosa, Montvale, N.J.; Jeannie Gerth, Brooklyn, N.Y.; Patricia A. Moore, Montvale; Stephen Russak, Hoboken, both of N.J.; Tamara Thomsen; Tucker Viemeister, both of New York, N.Y.

[73] Assignee: McNeil-PPC, Inc., Milltown, N.J.

[21] Appl. No.: 548,787

[22] Filed: Jul. 6, 1990

[51] Int. Cl.⁵ .............................................. A61F 13/15
[52] U.S. Cl. .................................. 604/386; 604/358; 604/385.1
[58] Field of Search ...................... 604/385.1, 386, 387, 604/392, 393, 397, 398, 400

[56] References Cited

U.S. PATENT DOCUMENTS 4,936,839 6/1990 Molee et al. ................... 604/385.1

Primary Examiner—Randy C. Shay
Assistant Examiner—G. Gualtieri

[57] ABSTRACT

Absorbent products, such as sanitary napkins are provided which include pocket means disposed on an undergarment-facing side of a central absorbent element. The products further include tab means extending laterally from one of the longitudinally extending sides of the absorbent element for a distance greater than about a width of the absorbent element and sized to be partially inserted into the pocket means after being wrapped around the crotch area of the undergarment for aiding in securing the sanitary napkin to an undergarment.

20 Claims, 3 Drawing Sheets

FIG. I

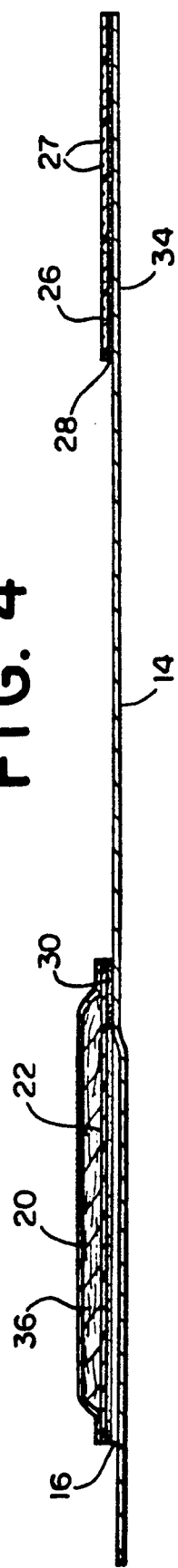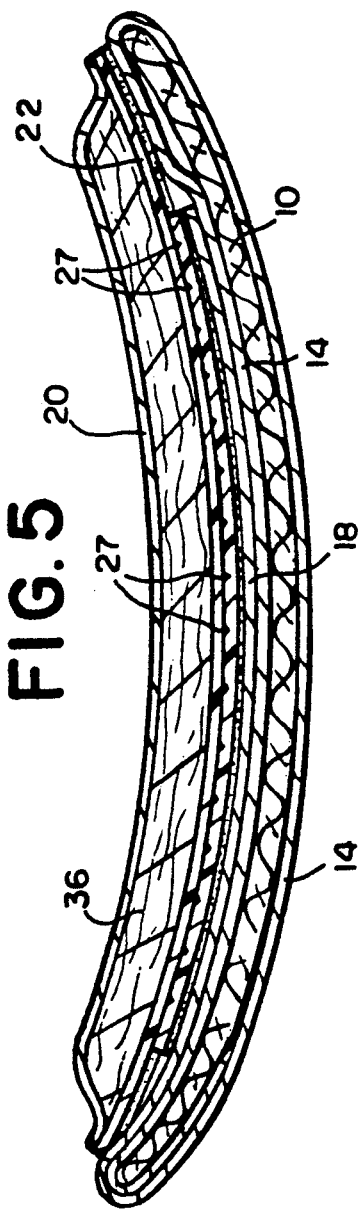

ABSORBENT PRODUCTS HAVING INTEGRAL TRANSVERSE RETAINING TAB AND POCKET

FIELD OF THE INVENTION

This invention relates to absorbent products for absorbing body fluids, and in particular, to means for applying such products against the perineal portion of the body and for holding them in place by securing them to the crotch portion of an undergarment. Such products find wide application as sanitary napkins, panty shields, panty liners and adult incontinence pads.

BACKGROUND OF THE INVENTION

In order to insure that a sanitary napkin performs its function effectively, it is important for the absorbent surface of the product to be properly exposed to the fluid being absorbed. Maximum absorptive efficiency is achieved when the napkin conforms to the perineal area of the user's body and is urged against the user's body by the undergarment. In conventional sanitary napkins having wood pulp absorbent elements, the sizable bulk of the product aids in conforming the absorbing surface to the perineal area. With such products, longitudinally disposed, pressure-sensitive adhesive strips have provided adequate adherence to the undergarment.

However, recent advances in absorbent technology, such as thin absorbent layers containing superabsorbents or peat moss boards, have reduced the thickness of sanitary napkins and other absorbent products. The reduced cross-sectional area and bulk of these improved products results in less resistance to twisting, folding and bunching, thereby resulting in a loss of product effectiveness. As the user goes about ordinary movements, the napkin becomes twisted or otherwise oriented in less than an optimal position. This condition causes both user discomfort and loss of absorptive efficiency.

Accordingly, there is a need for an improved securement means for absorbent products, such as ultra-thin sanitary napkins, for keeping them in substantial conformance with both the perineal region of the body and the user's undergarment. Such a securement means should reduce the twisting and disorientation that absorbent products often undergo if held to the undergarment merely by strips of adhesive.

SUMMARY OF THE INVENTION

Sanitary napkins, and other products, are provided by this invention which include a central absorbent element having a body-facing side and an undergarment-facing side. Disposed on the undergarment-facing side of the central absorbent element is a pocket means. Extending laterally from one of the sides of the central absorbent element is a tab means which has a lateral length greater than about the width of the absorbent element and is sized to be partially inserted into the pocket means after being wrapped around a crotch area of the undergarment.

Accordingly, secure attachment to undergarments can be provided by the integral tab and pocket arrangement of this invention. The tab and pocket elements preferably provide an interlocking and frictional fit, which enables the napkin to be supported over a broad surface area of the undergarment. Thus, even when this system is used in association with ultra-thin sanitary napkins, art-recognized problems such as shifting and bunching can be minimized.

The tab and pocket arrangement of this invention can be cost-effectively produced by using, as part of its construction, the conventional body-fluid impervious surface found on most sanitary napkins. More preferably, a single sheet of thermoplastic material attached to the body-fluid impervious surface can be used to construct a portion of the pocket as well as a portion of the laterally extending tab to facilitate manufacturing, minimize cost, and improve the integral strength of the overall product. The tab and pocket members of this invention can be supplemented with rigid or semi-rigid materials for providing even more support to the combined pocket and tab structure.

BRIEF DESCRIPTION OF THE DRAWINGS

The accompanying drawings illustrate preferred embodiments of the invention for the practical application of the principles thereof, and in which:

FIG. 4: is an enlarged cross-sectional view, taken through line 4—4 of FIG. 1, illustrating the component parts of a preferred sanitary napkin of this invention with its integral tab member and pocket means; and FIG. 5: is an enlarged, cross-sectional view, taken through line 5—5 of FIG. 2, illustrating how a preferred tab member is wrapped around the crotch portion of an undergarment and inserted into a preferred pocket.

DETAILED DESCRIPTION OF THE INVENTION

This invention provides absorbent products, such as sanitary napkins, panty shields, panty liners and adult incontinence pads. The elements of the invention will be described, however, with respect to sanitary napkin embodiments in order to simplify the description. The term "sanitary napkin" is, therefore, used generically to include all absorbent products worn against the perineal area of the body.

The sanitary napkins of this invention include a central absorbent element having longitudinally extending sides, transverse ends, a body-facing side and an undergarment-facing side. Disposed on the undergarment-facing side of the central absorbent is a pocket means, which is preferably a containment area having one or two openings therein. Disposed on and extending laterally from one of the longitudinally extending sides of the central absorbent element is a tab means which extends for a distance greater than about the width of the absorbent element. The tab means is sized to be partially inserted into the pocket means, after the tab means has been wrapped around a crotch area of an undergarment, for aiding and securing the sanitary napkin to the undergarment.

In further, more detailed, embodiments of this invention sanitary napkins are provided which include a central absorbent element having a body fluid impervious surface disposed on its undergarment-facing side and a thermoplastic sheet affixed to the body fluid impervious surface and forming a pocket therewith. The thermoplastic sheet extends a distance greater than about the width of the central absorbent element and comprises a semi-rigid, tapered tab member. Thus, the thermoplastic sheet of this embodiment defines a portion of both the pocket and tab means. The thermoplastic sheet is capable of being wrapped around an undergarment crotch portion, whereupon the tab member can be at least partially inserted into the pocket for securing the sanitary napkin to the undergarment.

This invention also provides a method for applying sanitary napkins to undergarments which includes providing a sanitary napkin having a central absorbent element and including tab means extending laterally from one of the longitudinally extending sides of the central absorbent element for a distance greater than about the width of the central absorbent element. The method further includes disposing the sanitary napkin onto an inner crotch portion of an undergarment, wrapping the tab means around the crotch portion of the undergarment, and inserting a portion of the tab means into the pocket for securing the sanitary napkin to the undergarment.

Figure 1:
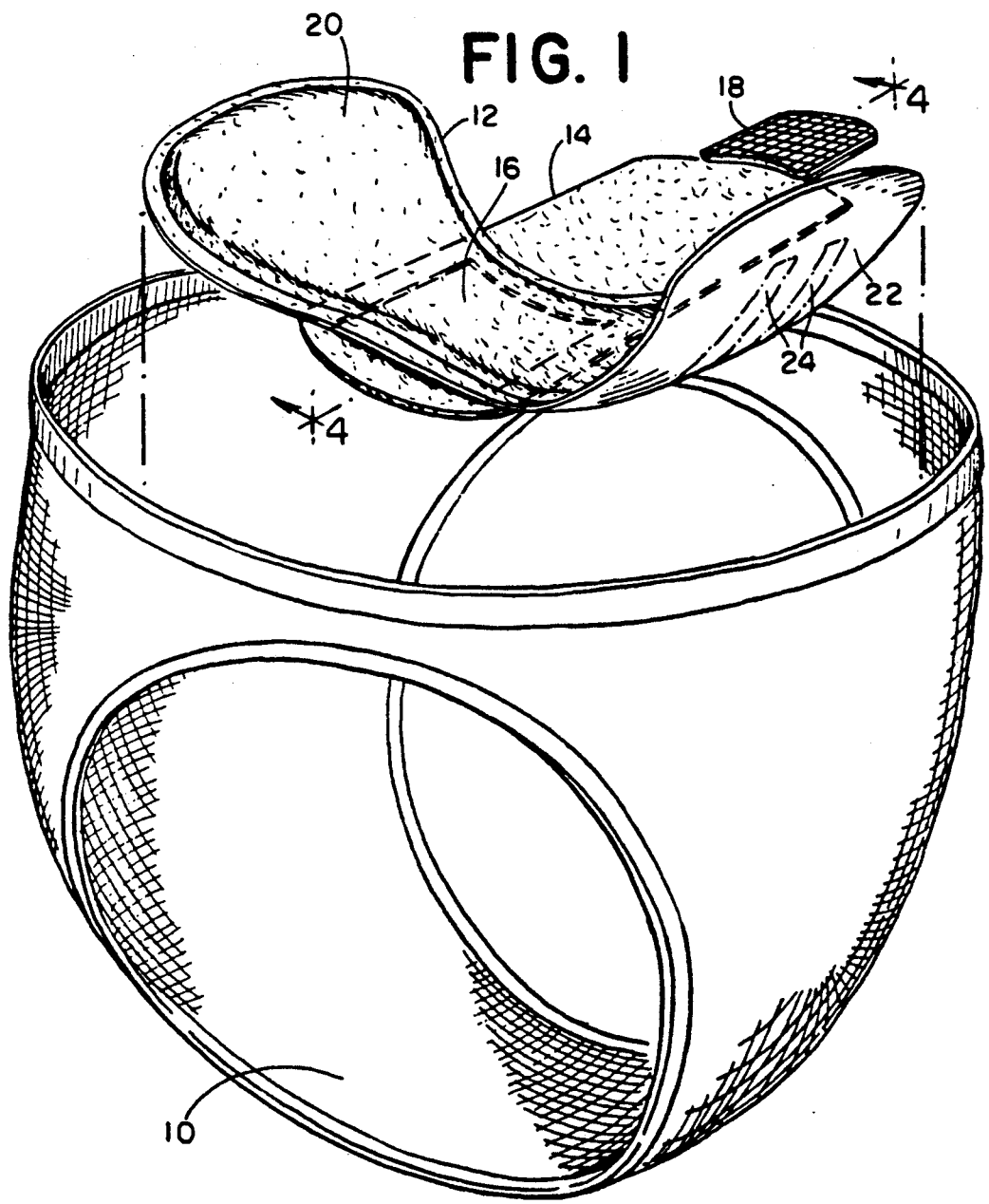
FIG. 1: is a perspective view of a preferred sanitary napkin of this invention having pocket and tab means and being applied to a crotch area of an undergarment.

With reference to the figures, and particularly to FIG. 1, there is shown a preferred sanitary napkin 12 being applied to an undergarment 10. The sanitary napkin 12 includes a body-facing side 20 for receiving body fluids, absorbent material 36, and an undergarment-facing side 22, which is preferably impervious to body fluids. The napkin 12 includes longitudinally extending, adhesive elements 24, which are like those traditionally employed for securing napkins and other products to undergarments. The napkin 12 further includes pocket means disposed on the undergarment-facing side 22 of the central absorbent element. The pocket means in the preferred embodiment includes a thermoplastic sheet 14 which is thermally, sonically, and/or adhesively attached to the body fluid impervious surface 22 to form pocket 16.

The pocket 16, although described as having a single opening, can also be fabricating by affixing two opposing portions of the thermoplastic sheet 14 to the body fluid impervious surface to form a slot having two openings therein. The thermoplastic sheet 14 also includes tab means, preferably tab member 18. It is understood that the tab member 18 can either be an integral portion of the thermoplastic sheet 14, or a separate element of the napkin 12 which is disposed laterally from one of the longitudinally extending sides of the napkin 12.

Figure 3:
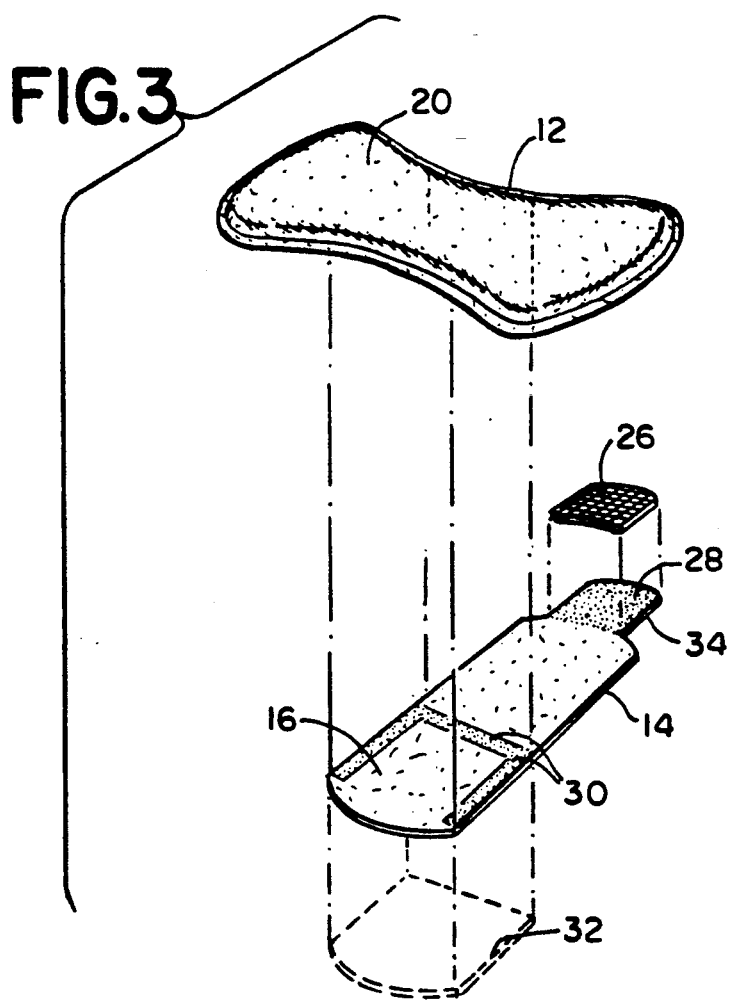
FIG. 3: is an exploded perspective view of a preferred sanitary napkin of this invention illustrating a central absorbent element, a thermoplastic sheet having a tab member and adhesive elements for defining a pocket with the undergarment-facing side of the central absorbent element, a semi-rigid scored layer being applied to the tab member, and a pocket reinforcing member, illustrated in phantom, being disposed on an undergarment-facing side of the pocket.

With reference to FIG. 3 and 4, exploded and cross-sectional views of the preferred sanitary napkin of this invention are illustrated. The napkin 12 is shown being adhesively applied to the thermoplastic sheet 14 with adhesive line 30 forming an integral pocket with the undergarment-facing side 22 of the sanitary napkin 12. Tab member 18 is shown as being a construction formed by an integral, tapered extension 34 of the thermoplastic sheet 14, which is adhered to a semi-rigid portion 26 with adhesive element 28. This embodiment can further include a rigid or semi-rigid reinforcing member 32, shown in phantom, which is preferably adhesively attached to an underside portion of the pocket 16.

Figure 2:
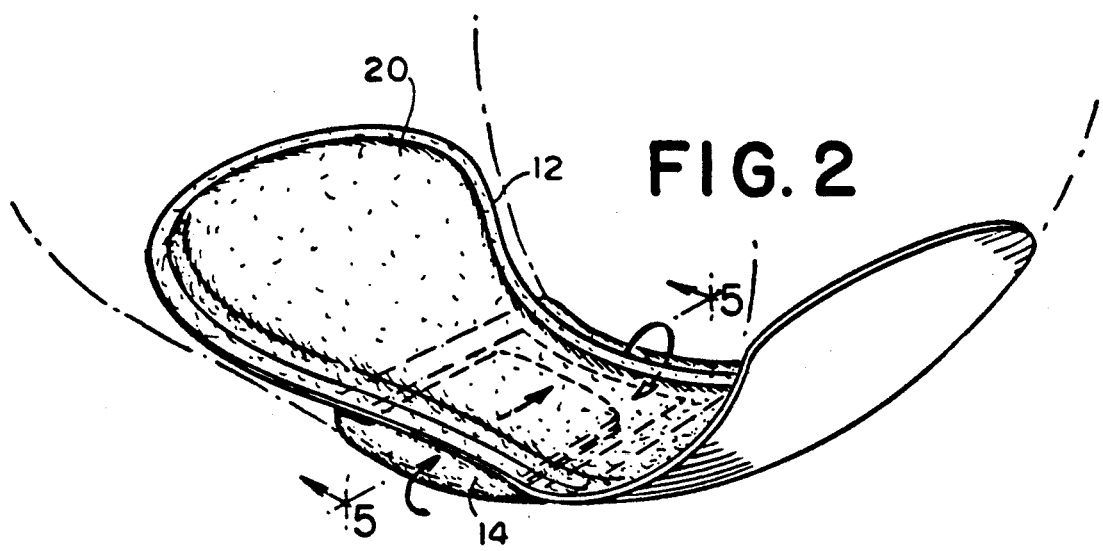
FIG. 2: is a partial perspective view of the undergarment and sanitary napkin of FIG. 1, illustrating how the sanitary napkin is adhesively applied to the inner crotch area of the undergarment, while the tab means is wrapped around the outer portion of the undergarment crotch area and inserted into the pocket means to further secure the napkin.

With reference to FIGS. 2 and 5, there is shown in perspective and cross-sectional views, the preferred sanitary napkin 12 of this invention being applied to an undergarment 10. The napkin 12 is first, preferably adhesively adhered to an inner crotch portion of the undergarment with adhesive strips 24. The integral thermoplastic sheet 14 is then extended laterally from the central absorbent element and wrapped around the outer crotch portion of the undergarment as described by the directional arrows in FIG. 2. A portion of the tab means, preferably tab member 18 is then inserted into the pocket 16 to complete the attachment process.

As illustrated in FIG. 5, the entire circumferential surface area of the undergarment crotch section is mechanically secured to the napkin 12 by the thermoplastic sheet 14. The tab member 18, preferably consisting of a tapered extension 34 of the thermoplastic sheet 14, adhesive element 28, and semi-rigid material 26, is inserted into pocket 16 after being wrapped around the undergarment 10. Score lines 27, applied to the semi-rigid material 26, increase the frictional resistance of this material and form a frictional fit against the body-fluid impervious portion of the undergarment-facing side 22 or other interior pocket surface. The rigidity of semi-rigid material 26 and increased frictional resistance provided by score lines 27 increase the integrity of the tab member and pocket joint. Moreover, score lines 27 further improve the product by permitting greater flexibility to the tab member, and hence, extra comfort to the wearer during use. Preferred materials and constructions of the sanitary napkins of this invention will now be described.

The central absorbent elements of this invention may be constructed with any of the well known absorbent materials used in products for absorbing body fluids such as, for example, loosely associated absorbent hydrophilic material such as cellulose fibers, e.g., wood pump, regenerated cellulose or cotton fibers. Such fibers may be chemically or physically modified and the absorbent element may include such fibers in combination with other materials, both natural, such as sphagnum moss, and synthetic, such as hydrophilic foams, hydrophilic polymers or the like.

The central absorbent element may also comprise layers of materials which in the aggregate are body fluid absorbent. For example, the outermost layer (closest to the body) may be a resilient, relatively non-absorbing, fluid previous material. Such a material is provided for comfort and conformability and directs fluid to an underlying layer, e.g. peat moss board or wood pulp, which retains such fluid. A useful material for this outer layer is hollow polyester fibers having a denier of about 8.5 and a length of about 1.5 inches.

Overlying the body-facing side of the central absorbent elements of this invention preferably is a fluid permeable cover material. This cover material may comprise any of the well known liquid pervious materials used in sanitary napkins including, for example, non-woven fabrics of cellulose, regenerated cellulose, polyester, polyethylene, or other synthetic polymers. Additionally, polymeric fibers or films having apertures therethrough to render the materials pervious to fluids may also by employed. A cover material of choice is a fabric comprising heat bondable polyester/-polyethylene conjugate fibers.

The central absorbent element, in accordance with a traditional design, can be wrapped in and adhered to an elongated C-shaped wrap or cover of fluid impervious material. See. U.S. Pat. No. 4,701,178 (FIG. 2) which patent is hereby incorporated by reference. The fluid impervious material preferably comprises a polyethylene "boat" which is adhered to the central absorbent element by an emulsion adhesive. The purpose of the polyethylene boat is fluid containment, whereby fluid will not be transferred from the undergarment-facing side and edges of the central absorbent element to an outer location where it could stain the undergarments of the user. The preferred polyethylene boat extends beyond the longitudinal ends of the central absorbent element. The boat is preferably heat or sonically sealed at the ends and adhered to a body fluid impervious barrier which constitutes the undergarment-facing side of the napkins. The barrier is provided to preclude body fluid from passing onto the undergarment of the wearer. The barrier, like the boat, may be any polymeric film such as a polyethylene, polypropylene, or cellophane or may be a normally fluid-pervious material that has been treated to be impervious such as a fluid repellent paper. When the boat and the barrier are made of heat bondable materials the boat may be advantageously thermally or ultrasonically sealed at its ends and to the barrier.

The preferred napkins of this invention can also include flaps, or side panels, which preferably extend out from the longitudinal edges of the barrier. The flaps can include absorbent and barrier layers and preferably extend a sufficient degree to enable them to overlie the outer crotch portion of the wearer's undergarment. They may also be constructed of a sufficient lateral length so that they overlap each other after they are wrapped around the crotch area of the undergarment. With flaps extended in this fashion, adhesive elements attached to the flap or flaps can be used to attach the flaps to one another. See U.S. Pat. No. 4,608,047, which is herein incorporated by reference. Flaps protect the user's undergarment from liquid escaping from the central absorbent element along its longitudinal edges and to act as an attachment system, in conjunction with the mechanical attachment means of this invention, to hold the central absorbent element firmly in place as it moves together with the crotch of the undergarment during the wearer's movements.

When the absorbent layer and the barrier material of the central absorbent element are both formed of thermoplastic material as described above, the napkin may be advantageously assembled by heat sealing or ultrasonic sealing. The absorbent layer of the flaps preferably is thermally sealed to the opposing longitudinal edges of the cover, and the barrier material of the flaps is thermally sealed to the opposing edges of the barrier of the central absorbent element. In a preferred embodiment, the barrier and the barrier material comprise sheets of 1.5 mil, embossed polyethylene.

The preferred adhesive elements of this invention preferably include pressure-sensitive adhesive. While such adhesive means are illustrated in the form of longitudinally extending lines, it will be understood that various patterns such as spots, squares, or transverse lines are suitable. The adhesive employed may be any of the large number of pressure-sensitive adhesives that are commercially available, including water-based adhesives such as acrylate adhesives, e.g., vinyl acetate/2-ethylhexyl acrylate copolymer which may be combined with tackifiers. Alternatively, the adhesive may also comprise a pressure-sensitive rapid-setting hot melt adhesive such as Fuller 6680 produced by the H. B. Fuller Co. The adhesive means may also comprise a double faced tape.

In another preferred embodiment of this invention an hourglass-shaped, ultra-thin, sanitary napkin is provided having a light-weight construction. In such an embodiment, the C-shaped boat and bulky wood pulp core are eliminated and a longitudinally-cut, absorbent layer, having a preferred thickness of less than about 10 mm, preferably less than about 5 mm, is employed. See U.S. patent application Ser. No. 242,273, entitled "Unitized Sanitary Napkin", filed on Sept. 12, 1988, now abandoned, and which is hereby incorporated by reference. The preferred absorbent layer of this embodiment includes a plurality of longitudinally extending absorbent strips, preferably made of superabsorbent material and/or peat moss. The layer also includes fibrous members for connecting the absorbent strips to one another along their longitudinal sides for maintaining the integrity of the layer during handling, i.e., processing, assembly, and use by the wearer. The layer be creped to achieve transverse creases which add more flexibility to the element and attendant comfort to a wearer. The absorbent layer is preferably sandwiched between an embossed fluid permeable cover, such as a non-woven layer of cellulose or polyester-polyethylene congregate fibers, and a polyethylene, fluid impervious barrier. The cover and barrier, which can include constructions and materials previously disclosed above, are then heat or ultrasonically sealed about the periphery of the hourglass-shape to seal in the absorbent layer. Flaps can also be provided in this light construction by extending the barrier and cover laterally from the central absorbent and then heat sealing and cutting these members in the form of flaps. The construction thus described is substantially thinner than the conventional sanitary napkin described earlier, and can be an attractive alternative product.

The foregoing demonstrates that the attachment mechanisms of this invention can provide securement of sanitary napkins to undergarments over a broad surface area for minimizing shifting during movements by a wearer. The tab and pocket arrangements of this invention can be favorably employed with ultra-thin sanitary napkins without the art-recognized bunching and twisting associated with employing only adhesive strips. Although various embodiments have been illustrated, this was for the purpose of describing, but not limiting the invention. Various modifications, which will become apparent to one skilled in the art, are within the scope of this invention described in the attached claims.

What is claimed is:

1. A sanitary napkin comprising:
    (a) a central absorbent element having longitudinally extending sides, transverse ends, a body-facing side and an undergarment-facing side;
    (b) pocket means disposed on said undergarment-facing side of said central absorbent element; and
    (c) tab means extending laterally from one of said longitudinally extending sides of said central absorbent element for a distance greater than about a width of said absorbent element and sized to be partially inserted into said pocket means after being wrapped around a crotch area of an undergarment for aiding in securing said sanitary napkin to said undergarment.

2. The sanitary napkin of claim 1 wherein said undergarment-facing side of said central absorbent element comprises a body fluid impervious surface, said body fluid impervious surface defining at least a portion of said pocket means.

3. The sanitary napkin of claim 2 wherein said pocket means comprises a thermoplastic sheet affixed to said body fluid impervious surface of said undergarment-facing side of said absorbent element.

4. The sanitary napkin of claim 3 wherein at least two opposing portions of said thermoplastic sheet are adhesively affixed to said body fluid impervious surface.

5. The sanitary napkin of claim 4 wherein said affixed thermoplastic sheet and said body fluid impervious surface define a containment area for securely receiving and retaining said tab means.

6. The sanitary napkin of claim 3 wherein said thermoplastic sheet defines a portion of said tab means.

7. The sanitary napkin of claim 6 wherein said tab means comprises a tab member extending laterally from an end portion of said thermoplastic sheet.

8. The sanitary napkin of claim 7 wherein said tab member comprises a semi-rigid portion.

9. The sanitary napkin of claim 8 wherein said semi-rigid portion of said tab member comprises a layer of semi-rigid material adhesively affixed to said tab member, said tab member further comprising a tapered extension of said thermoplastic sheet.

10. The sanitary napkin of claim 9 wherein said semi-rigid portion is scored in at least a first direction for improving the flexibility and for increasing the frictional resistance of said semi-rigid portion.

11. The sanitary napkin of claim 10 wherein said semi-rigid portion is also scored in a second direction.

12. The sanitary napkin of claim 1 wherein said central absorbent element comprises a calendered peat moss board.

13. The sanitary napkin of claim 12 wherein said board comprises a portion which has been subjected to a creping process.

14. A sanitary napkin comprising:
a central absorbent element having longitudinally extending sides, transverse ends, a body-facing side and an undergarment-facing side, said undergarment-facing side comprising a body fluid impervious surface; a thermoplastic sheet affixed to said body fluid impervious surface and forming a pocket therewith; said thermoplastic sheet extending a distance greater than about a width of said central absorbent element and comprising a semi-rigid, tapered, tab member; whereby said thermoplastic sheet is capable of being wrapped around an undergarment and said tab member is capable of being at least partially inserted into said pocket for securing said sanitary napkin to said undergarment.

15. The sanitary napkin of claim 14 wherein said tab member comprises resistance means for at least increasing the frictional resistance of said tab member when said tab member is inserted into said pocket.

16. A method of applying a sanitary napkin to an undergarment comprising:
   (a) providing a sanitary napkin comprising a central absorbent element having longitudinal extending sides, transverse ends, a body-facing side and undergarment-facing side, pocket means disposed on said undergarment-facing side, and tab means extending laterally from one of said longitudinally extending sides of said absorbent element for a distance greater than about a width of said absorbent element;
   (b) disposing said sanitary napkin onto an inner crotch portion of said undergarment;
   (c) wrapping said tab means around said crotch portion of said undergarment; and
   (d) inserting a portion of said tab means into said pocket for securing said sanitary napkin to said undergarment.

17. The method of claim 16 wherein said undergarment-facing side of said central absorbent element comprises a body fluid impervious surface, said body fluid impervious surface defining at least a portion of said pocket means.

18. The method of claim 17 wherein said pocket means comprises a thermoplastic sheet affixed to said undergarment-facing side of said central absorbent element.

19. The method of claim 18 wherein said sheet of thermoplastic material defines a portion of said tab means.

20. The method of claim 19 wherein said thermoplastic sheet is adhesively affixed to said body fluid impervious surface.

* * * * *